United States Patent [19]
Trautman et al.

[11] Patent Number: 6,083,196
[45] Date of Patent: Jul. 4, 2000

[54] DEVICE FOR ENHANCING TRANSDERMAL AGENT FLUX

[75] Inventors: Joseph Creagan Trautman, Sunnyvale; Michel J. N. Cormier, Mountian View; Hyunok Lynn Kim, Walnut, all of Calif.; Michael G. Zuck, Bend, Oreg.

[73] Assignee: ALZA Corporation, Mountain View, Calif.

[21] Appl. No.: 09/208,812

[22] Filed: Dec. 9, 1998

Related U.S. Application Data

[60] Provisional application No. 60/069,339, Dec. 11, 1997, and provisional application No. 60/069,340, Dec. 11, 1997.

[51] Int. Cl.$^7$ .................................................. A61B 17/20
[52] U.S. Cl. ............................ 604/46; 606/186; 600/556
[58] Field of Search ................................ 604/46, 47, 48, 604/117; 606/183, 186; 600/556

[56] References Cited

U.S. PATENT DOCUMENTS

| | | | |
|---|---|---|---|
| Re. 25,637 | 9/1964 | Kravitz et al. | 128/253 |
| 2,893,392 | 7/1959 | Wagner et al. | 128/253 |
| 3,072,122 | 1/1963 | Rosenthal | 128/253 |
| 3,675,766 | 7/1972 | Rosenthal | 206/63.4 |
| 3,814,097 | 6/1974 | Ganderston et al. | 128/268 |
| 3,964,482 | 6/1976 | Gerstel et al. | 128/260 |
| 4,340,048 | 7/1982 | Eckenhoff | 128/213 |
| 4,379,454 | 4/1983 | Campbell et al. | 604/897 |
| 4,588,580 | 5/1986 | Gale et al. | 424/21 |
| 4,655,766 | 4/1987 | Theeuwes et al. | 604/896 |
| 4,698,062 | 10/1987 | Gale et al. | 604/896 |
| 4,753,651 | 6/1988 | Eckenhoff | 424/449 |
| 4,756,314 | 7/1988 | Eckenhoff et al. | 128/760 |
| 4,832,953 | 5/1989 | Campbell et al. | 424/448 |
| 4,867,982 | 9/1989 | Campbell et al. | 424/449 |
| 5,080,646 | 1/1992 | Theeuwes et al. | 604/20 |
| 5,147,296 | 9/1992 | Theeuwes et al. | 604/20 |
| 5,169,382 | 12/1992 | Theeuwes et al. | 604/20 |
| 5,169,383 | 12/1992 | Gyory et al. | 604/20 |
| 5,242,406 | 9/1993 | Gross et al. | 604/132 |
| 5,250,023 | 10/1993 | Lee et al. | 604/20 |
| 5,268,209 | 12/1993 | Hunt et al. | 428/34.3 |
| 5,279,543 | 1/1994 | Glikfeld et al. | 604/20 |
| 5,279,544 | 1/1994 | Gross et al. | 604/20 |
| 5,310,404 | 5/1994 | Gyory et al. | 604/20 |
| 5,312,456 | 5/1994 | Reed et al. | 411/456 |
| 5,362,307 | 11/1994 | Guy et al. | 604/20 |
| 5,385,543 | 1/1995 | Haak et al. | 604/20 |
| 5,423,739 | 6/1995 | Phipps et al. | 604/20 |
| 5,438,984 | 8/1995 | Schoendorfer | 128/632 |
| 5,569,272 | 10/1996 | Reed et al. | 606/151 |

FOREIGN PATENT DOCUMENTS

| | | |
|---|---|---|
| 195 25 607 A1 | 1/1997 | Germany . |
| 2 221 394 | 2/1990 | United Kingdom . |
| WO 96/17648 | 6/1996 | WIPO . |
| WO 96/37155 | 11/1996 | WIPO . |
| WO 96/37256 | 11/1996 | WIPO . |
| WO 97/07734 | 3/1997 | WIPO . |
| WO 97/48440 | 12/1997 | WIPO . |
| WO 98/28037 | 7/1998 | WIPO . |

OTHER PUBLICATIONS

Haley, Thomas J., et al., Journal of Pharmaceutical Sciences, vol. 63, (1974), p. 106., "Instrument for Producing Standardized Skin Abrasions".

Eppstein, Jonathan, et al., presented at a conference sponsored by IBC in San Diego on Dec. 15–18, 1997, "Rapid Transdermal Drug Delivery with Thermal Micro–Poration".

Reiss, Susan M., Biophotonicks International, May/Jun. 1997, pp. 43–45, "Glucose– and Blood–Monitoring Systems Vie for Top Spot", Date Missing.

*Primary Examiner*—John D. Yasko
*Attorney, Agent, or Firm*—D. Byron Miller; Steven F. Stone

[57] ABSTRACT

A device (3) comprising a sheet member (6) having a plurality of microprotrusions (4) for penetrating the skin and a substantially incompressible agent reservoir housing (15) contacting and extending across the sheet member (6) for transmitting a hold-down force applied the sheet member (6) to maintain the microprotrusions (4) in skin-piercing relation to the skin, even during and after normal patient body movement.

29 Claims, 12 Drawing Sheets

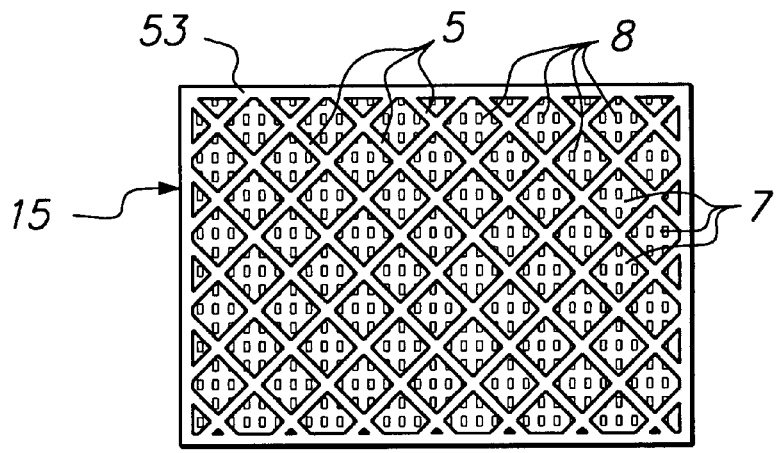
FIG. 8
FIG. 9
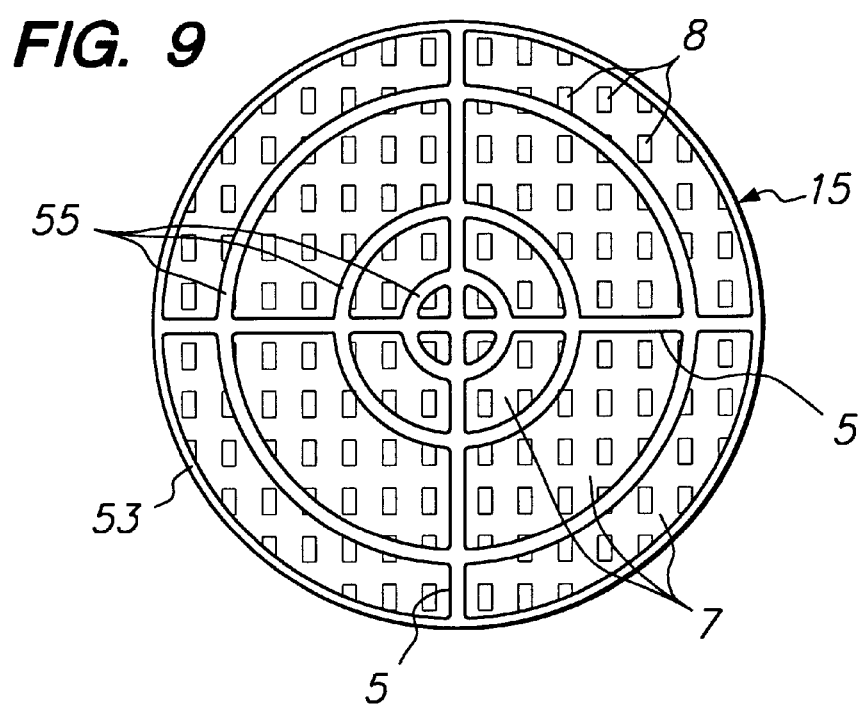

DEVICE FOR ENHANCING TRANSDERMAL AGENT FLUX

This application claims benefit of Provisional Appl. 60/069,339, filed Dec. 11, 1997 and Provisional Appl. 60/069,340 filed Dec. 11, 1997.

TECHNICAL FIELD

The present invention relates to transdermal agent delivery and sampling. More particularly, this invention relates to the transdermal delivery of agents, such as peptides and proteins, through the skin, as well as the transdermal sampling of agents from the body, such as glucose, other body analytes and substances of abuse, such as alcohol and illicit drugs.

BACKGROUND ART

Interest in the transdermal delivery of high molecular weight beneficial agents such as peptides, proteins and oligonucleotides to the human body continues to grow with the increasing number of medically useful peptides, proteins and oligonucleotides becoming available in large quantities and pure form. The transdermal delivery of peptides, proteins and oligonucleotides still faces significant problems. In many instances, the rate of delivery or flux of such agents through the skin is insufficient to produce a desired therapeutic effect due to their large size/molecular weight and the resulting inability to pass through natural pathways (pores, hair follicles, etc.) through skin. In addition, polypeptides and proteins are easily degradable during penetration of the skin, prior to reaching target cells. Likewise, the passive flux of water soluble small (e.g., 200 to 500 dalton) agent molecules is often limited.

One method of increasing the transdermal delivery of agents relies on the application of an electric current across the body surface or on "electrotransport". "Electrotransport" refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported. Electrotransport delivery generally increases agent delivery, particularly large molecular weight species (e.g., polypeptides) delivery rates, relative to passive or non-electrically assisted transdermal delivery. However, further increases in transdermal delivery rates and reductions in polypeptide degradation during transdermal delivery are highly desirable.

One method of increasing the agent transdermal delivery rate involves pre-treating the skin with, or co-delivering with the beneficial agent, a skin permeation enhancer. The term "permeation enhancer" is broadly used herein to describe a substance which, when applied to a body surface through which the agent is delivered, enhances its flux therethrough. The mechanism may involve a reduction of the electrical resistance of the body surface to the passage of the agent therethrough, an increase in the permselectivity and/or permeability of the body surface, the creation of hydrophilic pathways through the body surface, and/or a reduction in the degradation of the agent (e.g., degradation by skin enzymes) during electrotransport.

There have also been many attempts to mechanically disrupt the skin in order to enhance transdermal flux, such as, U.S. Pat. Nos. 3,814,097 issued to Ganderton et al., 5,279,544 issued to Gross et al., 5,250,023 issued to Lee et al., 3,964,482 issued to Gerstel et al., U.S. Pat. No. Re 25,637 issued to Kravitz et al. and PCT application WO 96/37155. These devices typically utilize tubular or cylindrical structures generally, although Gerstel does disclose the use of other shapes, to pierce the outer layer of the skin. The piercing elements disclosed in these references generally extend perpendicular from a thin flat member, such as a pad or metal sheet.

More recently, attempts have been made to anchor the tiny piercing elements of such devices in the skin in order to keep the drug transmitting pathways open, which pathways are cut through the stratum corneum by the microprotrusions. See for example, Cormier, et al., WO 97/48440. Unfortunately, because of the extremely small size of the microprotrusions, the formation of barbs and similar anchoring elements on the microprotrusions is problematic.

The microprotrusion arrays disclosed in WO 97/48440 are in the form of a thin metal sheet having a plurality of agent-transmitting openings therethrough. The sheet has a skin proximal surface and a skin distal surface. A plurality of etched and punched mircroprotrusions extend roughly perpendicularly from the skin distal surface of the sheet. A reservoir adapted to contain (in the case of agent delivery) or receive (in the case of agent sampling) the agent is positioned on the skin distal surface of the sheet. The microprotrusion array and the agent reservoir are then pressed onto the skin surface and maintained on the skin using an adhesive overlay or similar securing means as shown in FIG. 1. Thus, the sheet member 6 having the microprotrusions 4 extending from a skin distal surface thereof is placed on the skin with the microprotrusions 4 penetrating into the skin surface. The agent reservoir 27 is shown on the skin distal side of sheet 6. The structure is held in place on the skin 30 by an overlay 3 having adhesive coated on at least the peripheral surfaces 9 thereof.

The agent reservoir 27 in the FIG. 1 device tended to be composed of soft compliant materials such as gels. Such soft compliant, and even flowable, materials were preferred with sheet member 6 since the gel material could easily flow into the openings of sheet member 6 in order to come into direct contact with skin 30.

DESCRIPTION OF THE INVENTION

Unfortunately, when using structures such as that disclosed in FIG. 1, it was found that with normal patient body movement, the microprotrusions 4 eventually worked their way out of the skin 30, as shown in FIG. 2, thereby allowing the pathways cut through the stratum corneum to quickly heal and eventually close, making further agent delivery therethrough problematic. In part, the compressibility of the agent reservoir 27 contributed to this problem.

The present invention provides a device suitable for increasing transdermal flux. The device has microprotrusions which penetrate a body surface (e.g., skin) to enhance agent delivery or sampling. The device of the present invention is useful for introducing an aqent (e.g., a drug) into, or withdrawing an agent (e.g., a body analyte) from a body surface such as skin. The device includes a body surface piercing member having a plurality of microprotrusions which extend from a body surface proximal portion of the member. The microprotrusions are adapted to pierce the body surface to a depth of up to about 500 $\mu$m. Thus, when applied to the skin, the microprotrusions are adapted to at least pierce through the stratum corneum layer. The device further includes a housing which contains a reservoir for the agent to be delivered or sampled. The housing is either a separate element which contacts the piercing member, or is integral with the piercing member, and maintains the reservoir in agent-transmitting relation with the pierced body surface. The housing is characterized by having a compressibility, in a direction normal to the body surface, of less than about 250 $\mu$m. The device further includes a securing member for securing the device to the body surface.

In one aspect of the invention, the piercing member and the housing are separate elements. The piercing member comprises a thin sheet having a plurality of openings therethrough for transport of the agent therethrough. The sheet has a body proximal surface which is adapted to be placed against the body surface, said plurality of microprotrusions extending from the body proximal surface. The housing is adapted to extend across at least a portion, and preferably the entire, body distal surface of the sheet.

In another aspect of the invention, the piercing member comprises a thin sheet having a body proximal edge, with said plurality of microprotrusions adapted to be placed against said body surface. The plane of the sheet is oriented in roughly perpendicular relation to the body surface being pierced. The housing is comprising of a plurality of said sheets, fastened together in spaced apart relation, in order to create reservoir containing voids between the adjacent sheets.

Preferably, the housing has a compressibility, in a direction normal to the body surface being pierced, of less than about 50 $\mu$m. Most preferably, the housing is comprised of porous sintered high density polyethylene or an open cell polyurethane foam having a compressibility of less than about 25 $\mu$m and a void volume of about 10 to 60%.

The device of the present invention can be used in connection with agent delivery, agent sampling or both. In particular, the device of the present invention is used in connection with transdermal drug delivery, transdermal analyte sampling, or both. Delivery devices for use with the present invention include, but are not limited to, electrotransport devices, passive devices, osmotic devices and pressure driven devices. Sampling devices for use with the present invention include, but are not limited to, reverse electrotransport devices, passive devices, negative pressure driven, and osmotic devices.

BRIEF DESCRIPTION OF THE DRAWINGS

In the figures, like reference numerals refer to like elements in the several drawings.

FIGS. 6, 8 and 9 are top plan views of other embodiments of the incompressible housing and skin penetrating member, with the securing overlay removed for ease of illustration;

MODES FOR CARRYING OUT THE INVENTION

Figure 3:
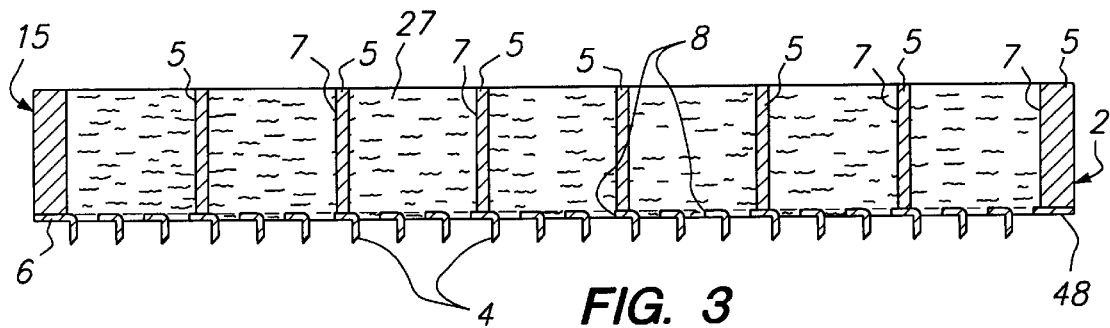
FIG. 3 is an enlarged cross-sectional view of an incompressible reservoir housing and skin penetrating member of the present invention taken along line III—III in FIG. 4.

Turning now to the drawings in detail, the device 2 of the present invention is generally shown in FIG. 3 comprising skin penetrating sheet member 6 and housing 15. Device 2 is used to enhance the transdermal delivery or sampling of an agent. The terms "substance", "agent" and "drug" are used interchangeably herein and broadly include physiologically or pharmacologically active substances for producing a localized or systemic effect or effects in mammals including humans and primates, avians, valuable domestic household, sport or farm animals, or for administering to laboratory animals such as mice, rats, guinea pigs, and the like. These terms also include substances such as glucose, other body analytes that are found in the tissue, interstitial fluid and/or blood, alcohol, licit substances, and illicit drugs, etc. that can be sampled through the skin.

The major barrier to the transdermal flux of agents (e.g., drugs to be delivered and analytes to be sampled) is the outermost layer of the skin (i.e., stratum corneum). The inner division of the epidermis generally comprises three layers commonly identified as stratum granulosum, stratum malpighii, and stratum germinativum. There is essentially little or no resistance to transport or to absorption of an agent through the stratum granulosum, stratum malpighii, and stratum germinativum. Device 2 comprises a rigid support member 15 and a compliant sheet member 6 (see FIG. 5 in which device 2 is in an inverted position to show the microprotrusions) having a plurality of microprotrusions 4 extending outwardly therefrom. The device 2 is pressed against an area of skin through which an agent is to be transdermally delivered or sampled. The microprotrusions 4 form tiny slits in the skin and penetrate at least through the stratum corneum so that the agent is conducted through the skin with little or no resistance. Typically, the microprotrusions penetrate the skin to a depth of up to 500 $\mu$m, more typically to a depth of 50 to 300 $\mu$m. The microprotrusions 4 can be microblades (FIGS. 3 and 5), pins (not shown), or any of a variety of configurations for piercing the skin or body surface. The microprotrusions 4 penetrate the stratum corneum of the epidermis when pressure is applied to the top (i.e., skin distal side) of the housing 15 to increase the administration of, or sampling of, an agent through a body surface. The term "body surface" as used herein refers generally to the skin, mucous membranes, and nails of an animal or human, and to the outer surface of a plant. The microprotrusions 4 penetrate the body surface to create good agent conduction from the system into the body, or vice versa.

Figure 4:
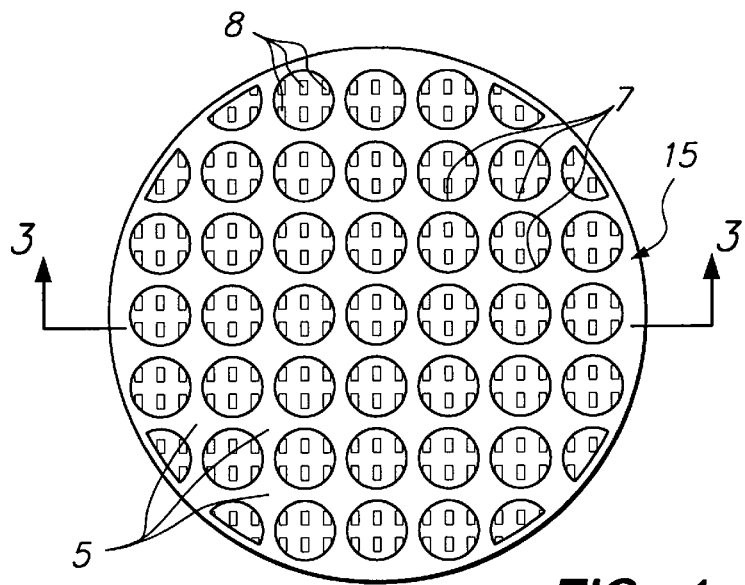
FIG. 4 is a top plan view of the device of FIG. 3, with the securing overlay removed for ease of illustration.
Figure 5:
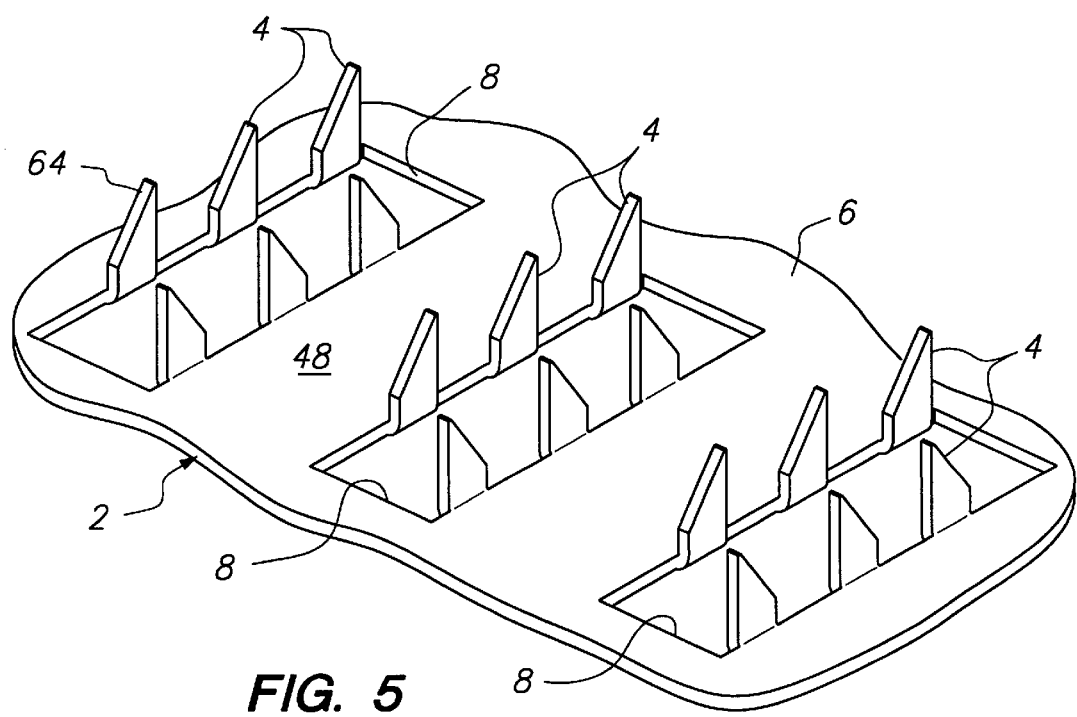
FIG. 5 is an enlarged perspective view of the bottom side of a skin penetrating member in accordance with one embodiment of the present invention.
Figure 6:
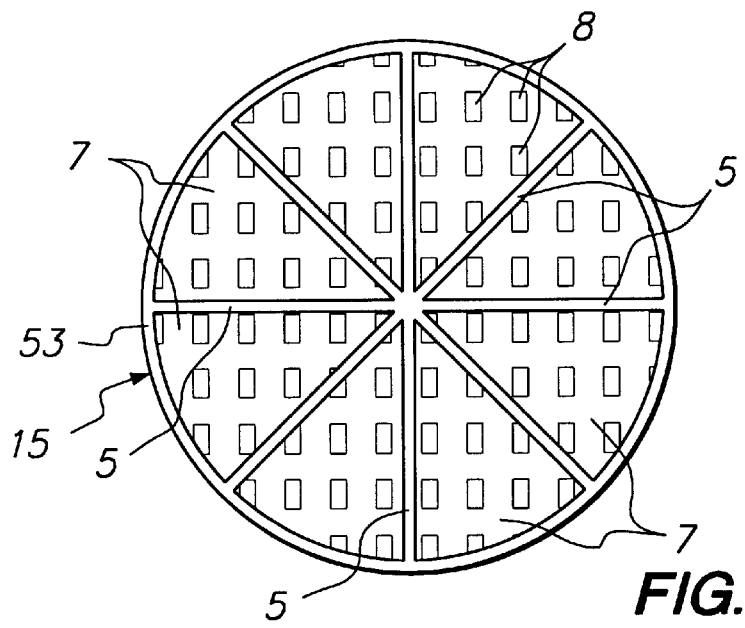

In the embodiments shown in FIGS. 3–5, the sheet member 6 is formed with a plurality of openings 8, each opening 8 having at least one microprotrusion 4 along the periphery thereof. The microprotrusions 4 cut microslits in the stratum corneum, thereby enhancing the transdermal flux of agent released from, or collected in, the agent containing or collecting reservoirs 27 housed by the plurality of voids 7.

Sheet member 6 can be composed of metal, silicon or plastic, although metals such as stainless steel and titanium are preferred. Sheet member 6 is generally compliant and flexible because of its relatively thin thickness. For example, when sheet member 6 is comprised of a metal such as stainless steel or titanium, the sheet member 6 will typically have a thickness of only about 5 $\mu$m to about 100 $\mu$m, and more typically about 25 $\mu$m to about 50 $\mu$m.

Figure 1:
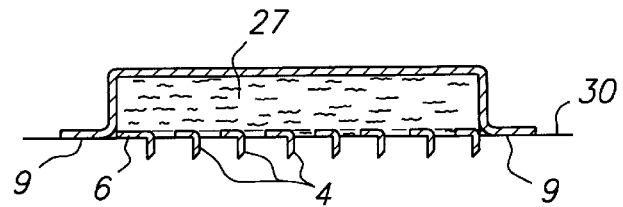
FIG. 1 is a cross-sectional view of a prior art device at the time of skin penetration.
Figure 2:
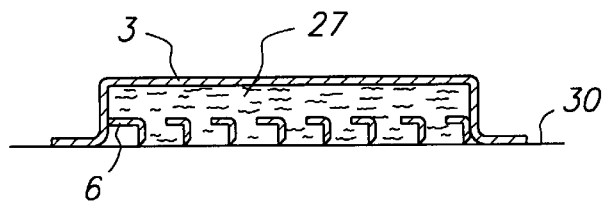
FIG. 2 is the device of FIG. 1 at a later point in time showing microprotrusion withdrawal from the body surface.
Figure 10:
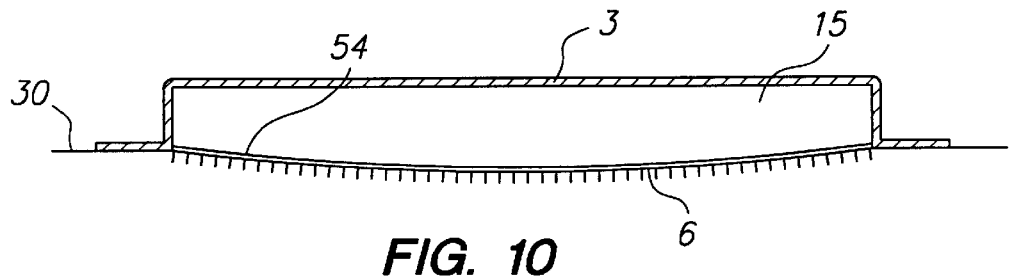
FIG. 10 is a side view of another embodiment of an incompressible reservoir housing and skin penetrating member in accordance with the present invention.

In accordance with the present invention, a substantially incompressible housing 15 is placed across the sheet member 6 (FIGS. 3 and 4). The housing 15 is then secured to the body surface with an adhesive securing overlay 3. The overlay 3 (FIGS. 7 and 10) is comprised of a sheet material which covers the housing 15 and extends beyond the peripheral edge of the housing 15 in order to make contact with the patient's skin 30. The device 2 is typically applied to the skin by pressing the device 2 into the skin, causing the tissue to become displaced. In this condition, the peripheral edge is of overlay 3 is adhered to the surface 30 of the skin surrounding device 2. Then the manually applied pressure is released causing the skin and underlying tissue to return partially to its original state. However, the overlay 3 holds the housing 15 tightly against the skin 30 causing the skin 30 to be in a partially displaced state, as best shown in FIG. 10. Because the housing 15 is substantially incompressible, the microprotrusions 4 are maintained in piercing relation with the body surface, even during normal patient movement. Thus, using the incompressible housing 1 5, the problem of prior art devices, namely the gradual withdrawal of the microprotrusions 4 from the skin as shown in FIG. 2, is avoided. Because the reservoir housing 15 is substantially incompressible, a secure hold down force can be applied by the securing overlay 3 without causing the agent reservoir material, which is typically comprised of a viscous liquid, gel or similar semisolid/soft material, to flow or otherwise deform thereby allowing protrusions 4 to withdraw from the skin as was the tendency with the prior art devices (FIGS. 1 and 2).

Housing 15 can be a variety of configurations, for example but not limited to the embodiments shown in FIGS. 3, 4, and 6–14. In the embodiment shown in FIGS. 3 and 4, housing 15 is an incompressible structure which forms a plurality of voids 7, extending through the thickness of the support member, which voids 7 collectively house reservoir 27 (FIG. 3) for containing the agent that is to be delivered or for receiving the agent that is to be sampled. Between the voids 7 are a plurality of supports or cross-members 5 which are in contact with and extend across the width or length of the sheet member 6. The cross-members 5 transmit the hold-down force that is applied to the top of the housing 15 by the overlay 3. When used with a transdermal electrotransport device, the sheet member 6 and/or housing 15 are preferably electrically isolated or insulated from the current conducting elements (e.g., the electrodes) of the electrotransport device in order to avoid short circuiting the drug reservoir. This can be achieved by using electrically insulative materials or coatings for sheet member 6 and/or housing 15.

The overlay 3 may be made of a sheet material which is either elastic or inelastic. Examples of inelastic sheet materials include polyethylene terephthalate films and other fabric reinforced polymer films. An example of an elastic overlay is Medpar™. Elastic overlay sheet materials are preferred.

As used herein, the term "incompressible" when referring to housing 15 means that the housing 15 is compressed to only a small degree in a direction normal to the skin surface, by the hold down force applied by the securing overlay 3. Preferably, the housing 15 compresses a distance of less than 250 $\mu$m, and more preferably less than 50 $\mu$m, when the hold down forced is applied by the securing overlay 3.

The housing 15 maybe made from any material having the aforementioned low compressibility. Suitable materials include metals, metal alloys, ceramics, glasses, incompressible plastics, incompressible polymeric foams, and incompressible reinforced (e.g., carbon fiber reinforced) polymers. A particularly preferred incompressible housing material is a porous sintered high density polyethylene sold under the tradename Porex® by Porex Technologies, Inc., of Fairburn, Ga.

The housing 15 may be either rigid or flexible, but preferably is flexible so that it more easily conforms to a patient body surface (e.g., the skin on a patient's arm). Preferably, when the housing 15 has a flat skin proximal surface, the housing 15 has the ability to flex into a curved configuration in response to the hold down force applied by the overlay 3. Most preferably, the housing 15 flexes (in response to the applied hold down force) to a degree such that the skin proximal surface of the housing 15 has a radius of curvature of less than about 10 cm. Alternatively, the housing can be arranged in individual rigid sections, adjacent sections being hingedly attached to one another.

Various embodiments of the reservoir housing 15 are illustrated in FIGS. 3–4 and 6–14. In the embodiments shown in FIGS. 3–4, 6–9 and 15, the housing 15 is comprised of a peripheral (e.g., annular) wall 53 having at least one cross-member 5 extending across the support member 15 so as to create a plurality of voids 7 which house the reservoir for the agent and to transmit the applied hold-down force substantially evenly across the sheet member 6 and without compressing the housing 15. The cross-members generally extend diagonally in FIGS. 6, 8 and 15 across the volume bounded by the outer wall of the housing 15. Diagonal, as used herein, is meant to describe embodiments other than cross-members joining two vertices of a rectilinear figure that are nonadjacent or passing through two nonadjacent edges of a polyhedron, as is apparent from the embodiments shown in the figures. As can be seen, the cross-members include oblique (FIG. 8) and non-oblique (FIG. 9) cross-members as well as honeycomb configurations (FIG. 4). The number of cross-members depends on a variety of factors, for example, the relative structural integrity or flexibility of the sheet member 6 and the housing 15, the distance across the housing 15, the size of the agent reservoir skin-contact area, and the volume of the agent reservoir. In general, when using sheet member 6 formed of very thin metal, the maximum distance between adjacent cross-members 5 in housing 15 will be no more than about 4 times, and preferably no more than about 2 times, the distance between adjacent microprotrusions 4 in sheet member 6. FIG. 9 illustrates that the housing 15 can be comprised of a plurality of inner annular walls 55 connected by the cross-members 5 to the outer annular wall 53.

Figure 7:
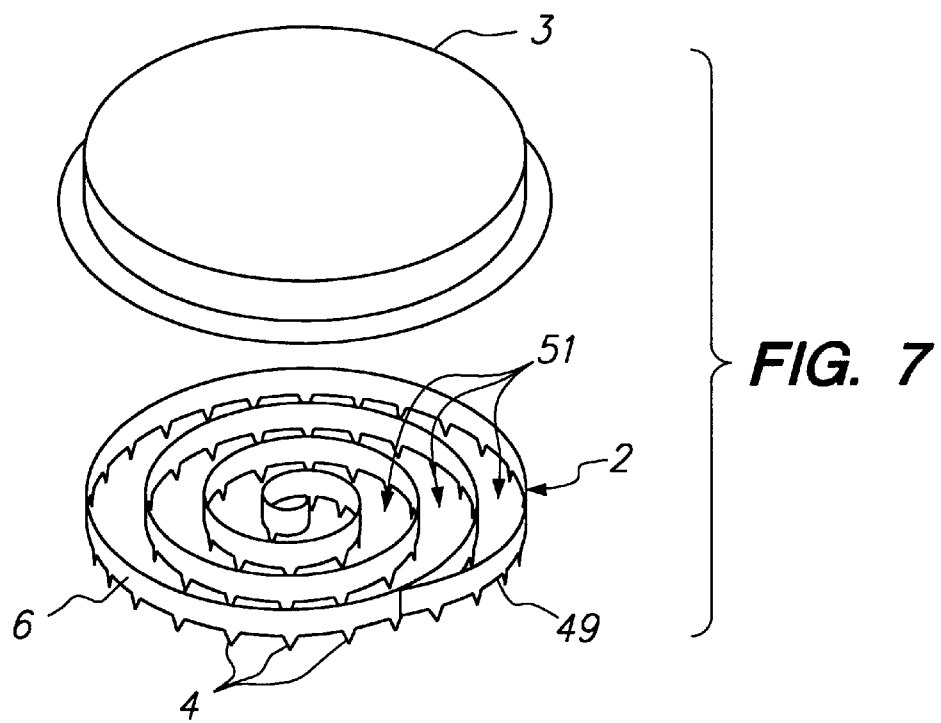
FIG. 7 is an exploded perspective view of an integral incompressible housing and skin penetrating member with a securing overlay.

FIG. 7 illustrates an alternate embodiment of the sheet member 6 wherein the microprotrusions 4 extend outwardly from a body contacting edge 49 of a thin, sheet member 6. In this embodiment, the plane of the sheet member 6 is oriented in approximately perpendicular relation to the body surface during use. The sheet member 6 has a spiral configuration which defines voids 51 for holding an agent-containing or an agent-receiving reservoir (not shown in FIG. 7). Coiling, folding (not shown), and curving (not shown) as well as other forms of forming the sheet member 6 from its generally planar state along its length to form a structure having a plurality of voids 51 can also be used. Thus, the sheet member 6 of FIG. 7 forms an integral agent reservoir housing and skin penetrating member.

Figure 21:
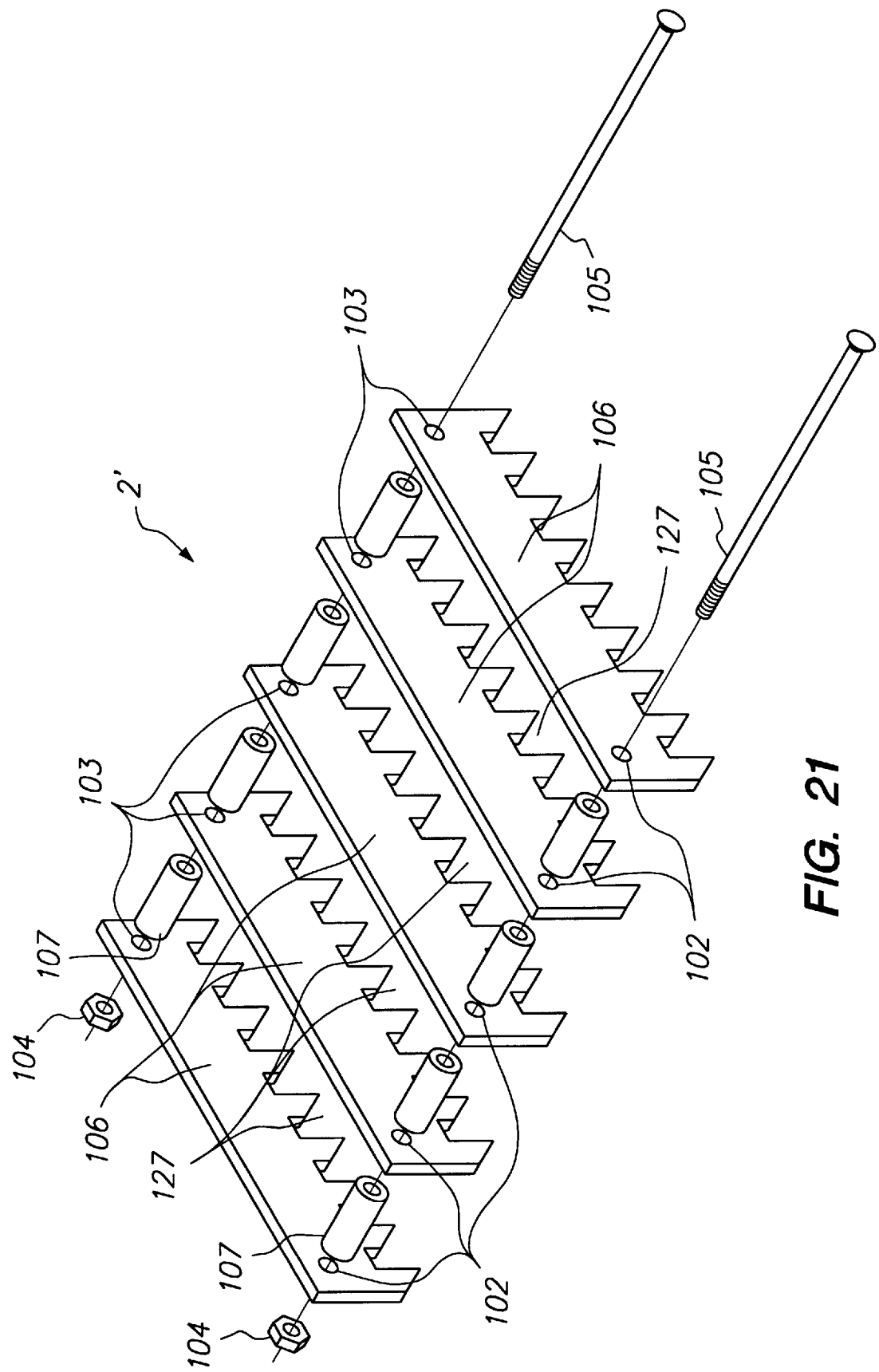
FIG. 21 is an exploded perspective view of another integral incompressible reservoir housing and skin penetrating member.

Like the integral housing/skin penetrating member of FIG. 7, FIG. 21 also shows an integral incompressible reservoir housing and skin penetrating member designated 2'. Each of the sheet members 106 has a pair of holes 102, 103, through which bolts 105 are inserted. Spacers (e.g., hollow cylindrical members or washers) 107 are positioned between the sheet members 106 to form voids 127 therebetween. The spaced sheet members 106 are held together as a unit by securing nuts 104 on the ends of bolts 105, or using other known fasteners. As in the FIG. 3 device, the voids 127 can be filled with a gel material adapted to contain the beneficial agent to be delivered or to receive the body analyte to be sampled. The individual sheet members 106, which are oriented roughly perpendicularly to the surface of the skin, are composed of a metal which is substantially incompressible in a direction normal to the skin surface. Thus, a hold-down force applied to the top/skin distal edges of sheet members 106 by an adhesive overlay 3 (not shown in FIG. 21), does not cause the sheet members to significantly compress in a direction normal to the skin surface.

Figure 14:
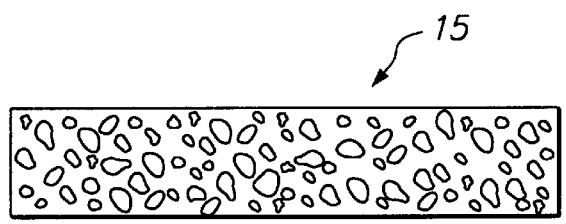
FIG. 14 is a perspective view of a preferred incompressible reservoir housing in accordance with another embodiment of the present invention.
Figure 15:
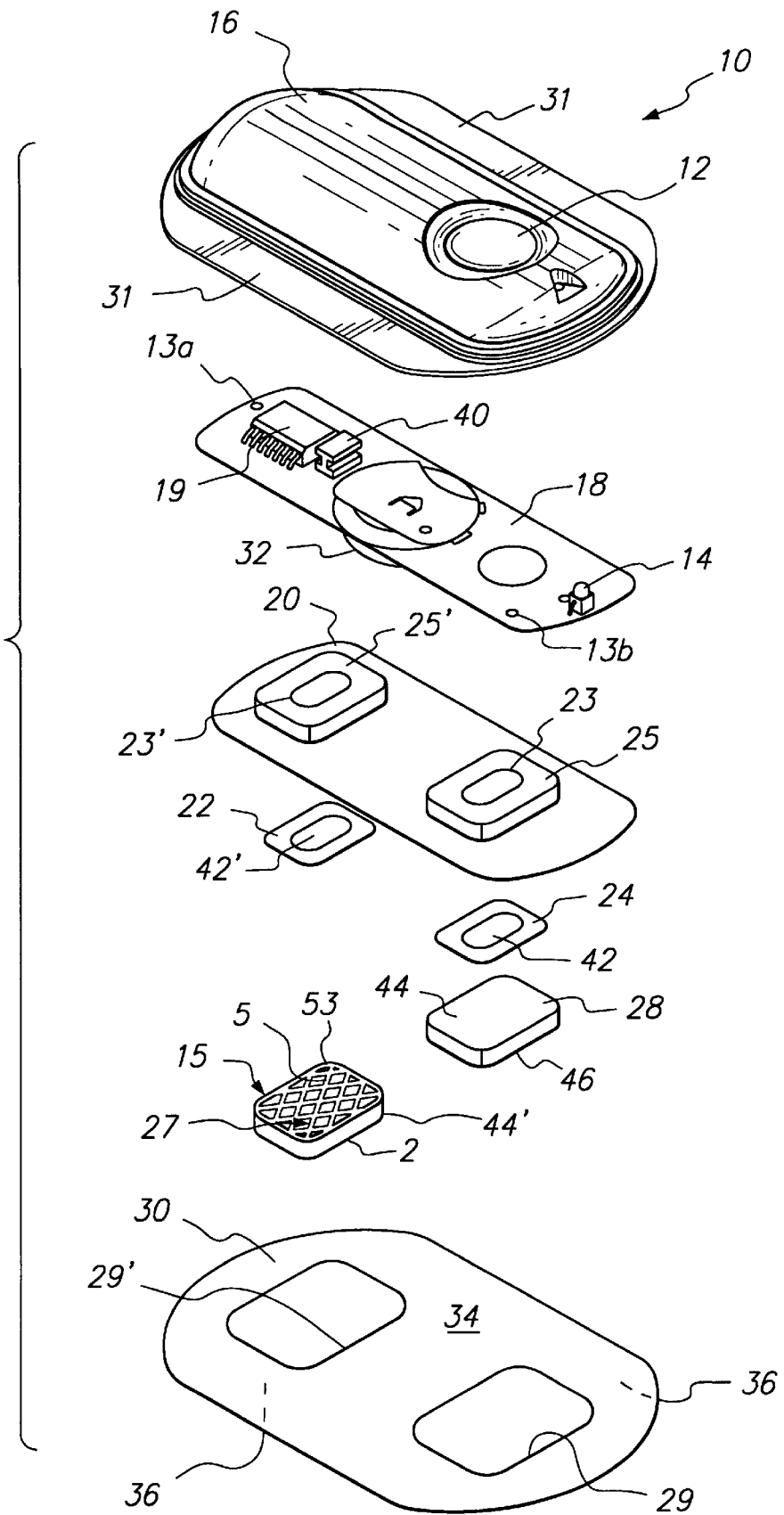
FIG. 15 is an exploded perspective view of an electrotransport agent delivery/sampling system according to one embodiment of the present invention.
Figure 16:
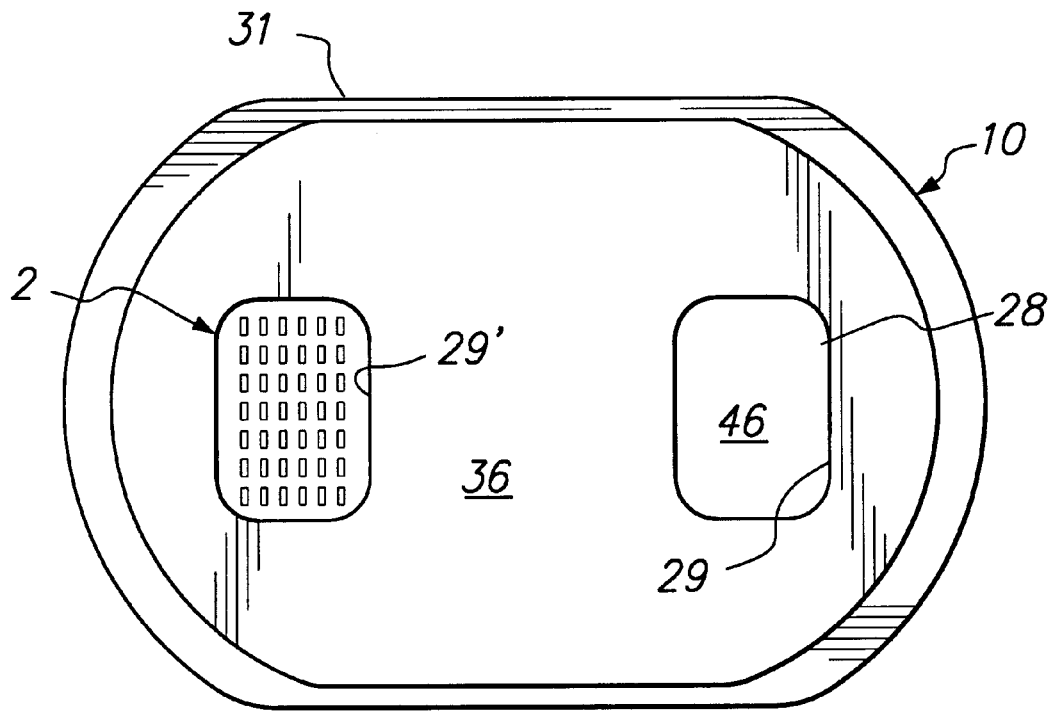
FIG. 16 is a bottom plan view of the electrotransport agent delivery/sampling system of FIG. 15.

The surface of housing 15 which contacts the skin distal side/edge of sheet member 6 is generally shown as flat (i.e., planar) in FIGS. 3 and 14. Most preferably however, the surface of housing 15 which contacts the sheet member 6 has a convex or curved (e.g., domed or cylindrically shaped) surface 54 as best shown in FIG. 10. The radius of curvature of the convex or cylindrically shaped surface 54 is preferably at least about 5 cm, more preferably at least about 10 cm.

Figure 11:
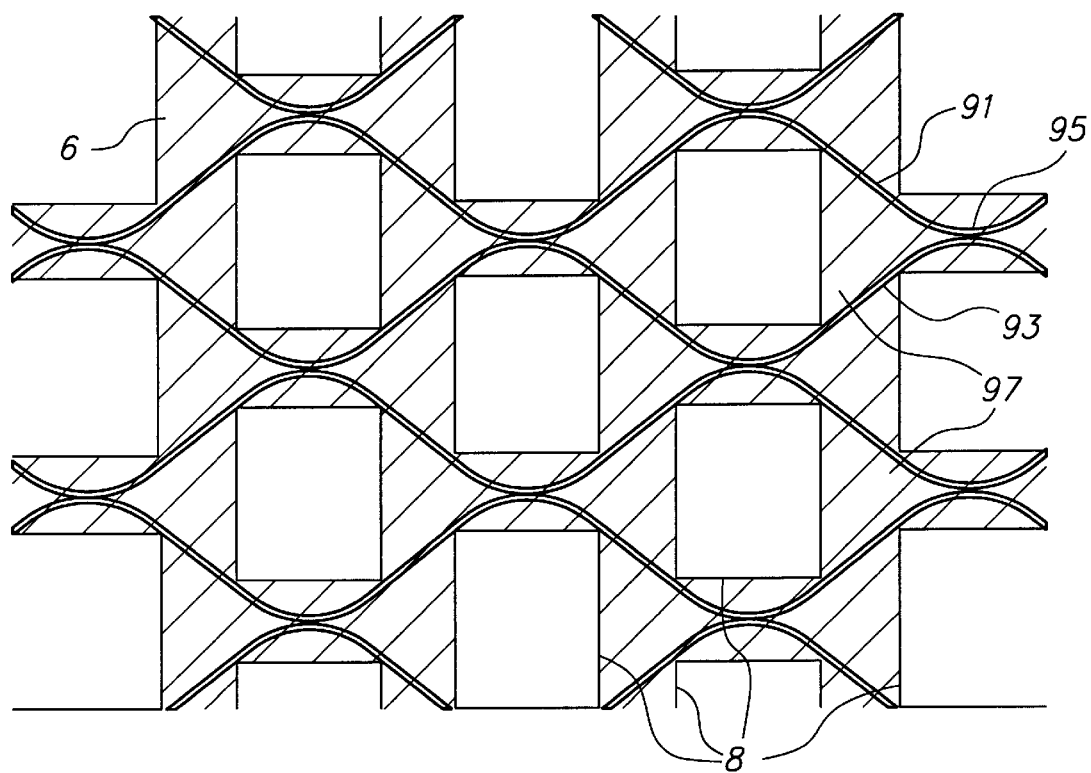
FIG. 11 is a top view of still another embodiment of the incompressible reservoir housing of the present invention with the securing overlay removed for ease of illustration.

FIG. 11 illustrates an alternate embodiment of the incompressible reservoir housing 15. In this embodiment, housing 15 is comprised of a plurality of strips which have a wavy (e.g., sinusoidal) shape and are oriented perpendicularly with respect to the plane of sheet member 6. Sheet member 6 has the same configuration shown in FIG. 5 with openings 8 therein and associated microprotrusions 4 (not shown in FIG. 11). The strips 91, 93 are preferably fixed together at their contact points 95 such as by welding in the case where the sheets 91, 93 are composed of metal or plastic. The configuration of the adjacent strips 91, 93 creates voids 97 therebetween for containing an appropriate reservoir material. Thus, the height of strips 91 and 93 will be governed in part by the volume, and hence the thickness, of the reservoir material loaded into voids 97.

Figure 12:
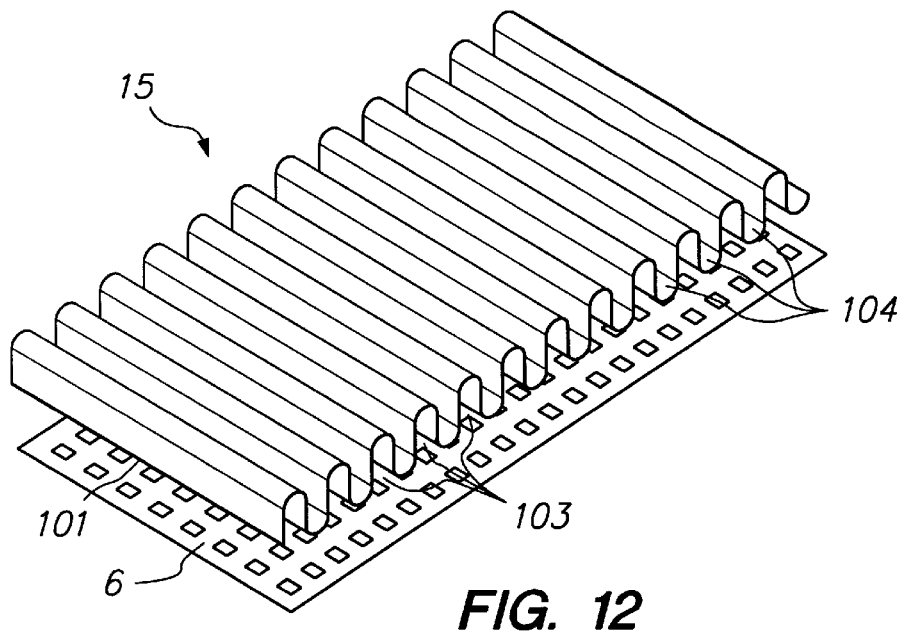
FIG. 12 is a perspective view of yet another embodiment of the incompressible reservoir housing of the present invention.

FIG. 12, illustrates yet another embodiment of incompressible reservoir housing 15. In this embodiment, housing 15 is comprised of a corrugated sheet 101. Corrugated sheet 101 is adapted to contact the skin distal side of sheet member 6. If necessary, a cover sheet (not shown in FIG. 12) covering the skin distal side of corrugated sheet 101, or rails (also not shown in FIG. 12) along the side edges of corrugated sheet 101, can be used to provide additional incompressibility and/or rigidity to prevent any tendency for the sheet 101 to bend or fold along the corrugation folds when a hold-down force is applied to the skin distal side of sheet 101. Optionally, corrugated sheet 101 may have a plurality of openings (not shown in FIG. 10) therein, thereby making it possible for agent to move through the corrugated sheet 101. The size and number of the openings may vary as long as the structural integrity and incompressibility of the corrugated sheet 101 is not compromised. The openings in the sheet 101 make it possible to place additional reservoir material into the voids 104 adjacent to the skin distal side of sheet 101. As in the other embodiments, a reservoir material can be loaded into the voids 103 formed between the corrugations and the underlying sheet member 6.

Figure 13:
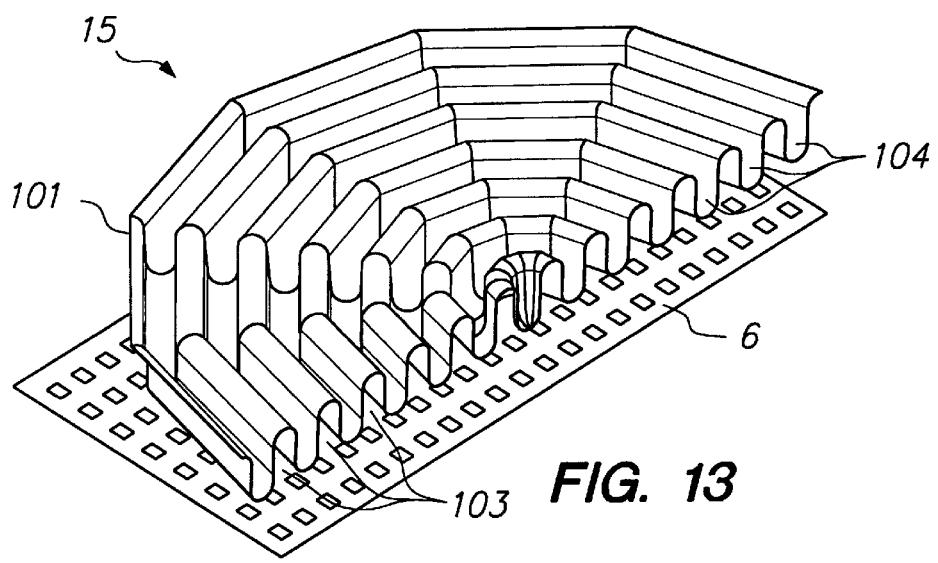
FIG. 13 is a perspective view of still another embodiment of the incompressible reservoir housing of the present invention.

FIG. 13 discloses an alternate embodiment of a corrugated sheet 101 in which the corrugation folds are not all parallel to one another. Similar to the device of FIG. 12, the FIG. 13 device can also be provided, if necessary, with a covering sheet over the skin distal side of corrugated sheet 101, or alternatively with an annular rail surrounding corrugated sheet 101, in order to enhance the structural incompressibility of corrugated sheet 101. Still further as in the FIG. 12 device, the FIG. 13 device can be provided with a plurality of openings (not shown in FIG. 13) in the corrugated sheet 101 in order to allow agent delivery therethrough. Such openings make it possible to utilizes voids 104 to contain agent reservoir material.

Yet another embodiment of the reservoir housing 15, illustrated in FIG. 14, comprises a flexible, porous yet substantially incompressible material such as porous sintered high density polyethylene. Such porous sintered high density polyethylenes typically have a void volume in the range of about 10 to 60%, and more preferably about 30 to 40%. A liquid solution, a gel or other semi-solid agent reservoir material can easily be introduced using known pumping techniques into the voids of such sintered porous materials. An example is Porex® sintered porous high density polyethylene sold by Porex Technologies of Fairburn, Ga.

The microprotrusions or microblades 4 are generally formed from a single piece of material and are sufficiently sharp and long for penetrating at least the stratum corneum of the skin. In one embodiment, the microprotrusions 4 and the sheet member 6 are essentially impermeable or are impermeable to the passage of an agent. The width of each microprotrusion can be any of a range of widths. The width of the microprotrusion at the intersection of the microprotrusion and the body surface after the microprotrusion array has been inserted is typically at least about 25 μm. The required length of the blades is subject to variation of the body surface being penetrated and corresponds to at least the natural thickness of the stratum corneum, for one of the principal features of the invention is that the microprotrusions are to penetrate at least through the stratum corneum and into the epidermis. Usually, the microprotrusions will have a length and configuration which achieves a depth of penetration of about 25 μm to about 400 μm, with the depth of penetration for most applications being between about 50 μm to about 200 μm. The microprotrusions 4 can have slanted (i.e., angled) leading edges 64 (FIG. 5) to further reduce the insertion force required to press the microprotrusions into the skin tissue. The leading edges of each microprotrusion 4 can all be the same angle or can be at different angles suitable for penetrating the skin. Alternatively, the leading edge of each microprotrusion can be curved having, for example, a convex or concave shape or be divided into any number of angled segments such as the first segment being relatively steep with respect to vertical and the second segment being more gradually angled with respect to vertical.

The sheet member 6 can be produced with a photolithography process followed by a chemical etching process followed by a micro-punching operation as disclosed in WO 97/48440, the disclosures of which are incorporated herein by reference. The embodiment of sheet member 6 illustrated in FIG. 7 requires an additional step of forming the planar sheet member 6 into the desired void-defining shape (i.e., spiral, serpentine, concentric circles, etc.). This can be accomplished using well-known metal sheet bending, rolling, folding and/or shaping techniques.

Generally, the microprotrusions 4 are at an angle of about 90° to the surface 48 (FIG. 5) of the sheet member 6 after being punched, but they can be disposed at any angle forward or backward from the perpendicular position that will facilitate penetration of the stratum corneum.

The sheet member 6 and microprotrusions 4 can be made from materials that have sufficient strength and manufacturability to produce microprotrusions, such as, glasses, ceramics, rigid polymers, reinforced (e.g., carbon fiber reinforced) polymers, metals and metal alloys. Examples of metals and metal alloys include but are not limited to stainless steel, iron, steel, tin, zinc, copper, gold, platinum, aluminum, germanium, zirconium, titanium and titanium alloys. Each of the sheet member and microprotrusions can have a thin layer of gold, platinum, iridium, titanium, or rhodium plating. Examples of glasses include silicas and devitrified glasses such as "PHOTOCERAM" available from Corning in Corning, N.Y. Examples of polymers include but are not limited to polystyrene, polymethylmethacrylate, polypropylene, polyethylene, "BAKELITE", cellulose acetate, ethylcellulose, styrene/acrylonitrile copolymers, stryrene/butadiene copolymers, acrylonitrile/butadiene/styrene (ABS) copolymers, polyvinyl chloride and acrylic acid polymers including polyacrylates and polymethacrylates.

The number of microprotrusions 4 and openings 8 of any of the embodiments of the sheet member 6 is variable with respect to the desired flux rate, agent being sampled or delivered, delivery or sampling device used (i.e., electrotransport, passive, osmotic, pressure driven, etc.), and other factors as will be evident to one of ordinary skill in the art.

An optional connecting medium (not shown) can be predisposed on the skin contacting side 48 of the sheet member 6 having the configuration shown in FIGS. 3–5 as taught in WO 98/28037, the disclosures of which are incorporate herein by reference. The connecting medium, if used, acts as a conduit for the agent and acts as a bridge between the agent containing or collecting reservoir and the skin, thus allowing an agent to be transported unhindered therethrough.

One type of transdermal delivery/sampling device, which can be used with the present invention relies on the application of an electric current across the body surface or "electrotransport". It will be appreciated by those working in the field that the present invention can be used in conjunction with a wide variety of electrotransport systems, as the invention is not limited in any way in this regard. For examples of electrotransport systems, reference may be had to U.S. Pat. Nos. 5,147,296 to Theeuwes et al., 5,080,646 to Theeuwes et al., 5,169,382 to Theeuwes et al., 5,423,739 to Phipps et al., 5,385,543 to Haak et al., 5,310,404 to Gyory et al., and 5,169,383 to Gyory et al., of which any of the disclosed electrotransport systems can be used with the present invention.

FIGS. 15–19 illustrate a representative electrotransport delivery/sampling device 10 that may be used in conjunction with a housing 15 and a skin penetrating device 2 in accordance with the present invention. Device 10 comprises an upper housing 16, a circuit board assembly 18, a lower housing 20, donor electrode 22, counter electrode 24, donor reservoir 27, counter reservoir 28 and skin-compatible adhesive 30. Upper housing 16 has lateral wings 31 which assist in holding device 10 on a patient's skin. Printed circuit board assembly 18 comprises an integrated circuit 19 coupled to discrete components 40 and battery 32. Circuit board assembly 18 is attached to housing 16 by posts 33 (only one shown in FIG. 17) passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 31. Shown (partially) on the underside of circuit board assembly 18 is a button cell battery 32. Other types of batteries may also be employed to power device 10 depending on the need.

Figure 17:
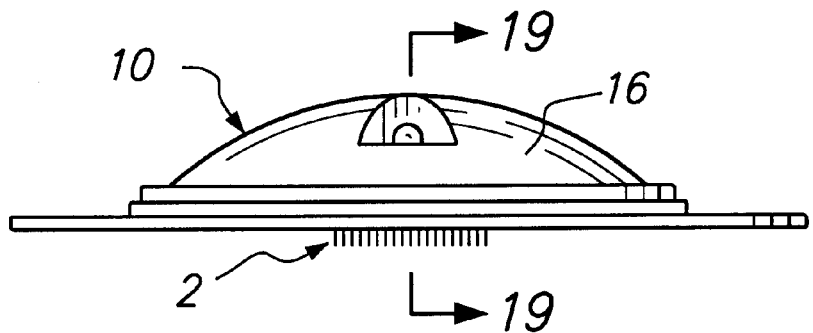
FIG. 17 is a right side elevational view of the electrotransport agent delivery/sampling system of FIG. 15.
Figure 18:
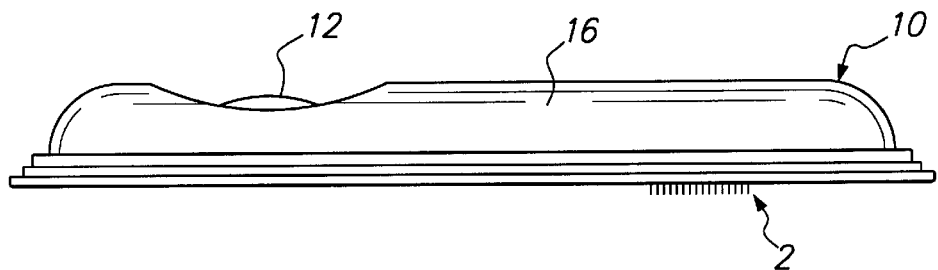
FIG. 18 is a rear elevational view of the electrotransport agent delivery/sampling system of FIG. 15.
Figure 19:
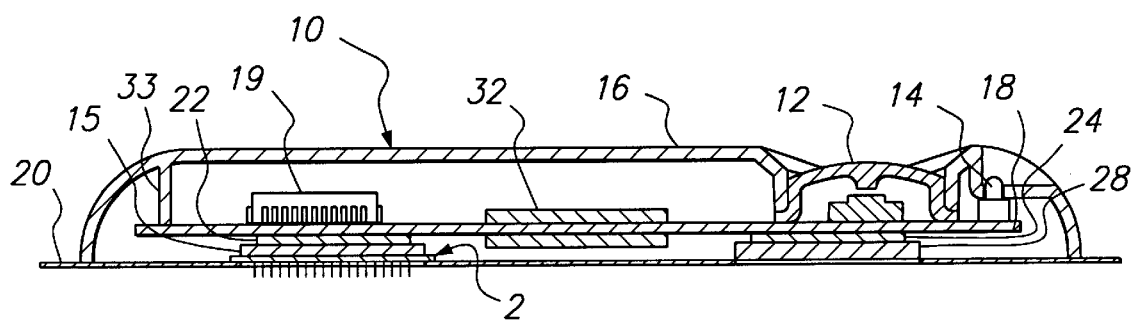
FIG. 19 is a cross-sectional view taken along line 19—19 of the electrotransport agent delivery/sampling system of FIG. 17.

The incompressible reservoir housing 15 of the present invention is sized and shaped to fit snugly within depression 25' in lower housing 20. The donor electrode 22 also fits within depression 25 adjacent the skin distal surface of reservoir housing 15. In this embodiment, it is important that electrode 22 also be comprised of substantially incompressible material such as a metallic foil. A sheet member 6 having a plurality of microprotrusions 4, similar to that shown in FIG. 5 is positioned adjacent the skin proximal surface of reservoir housing 15. Thus, when the device 10 is placed on the skin of the patient, the microprotrusions 4 extend downwardly and are adapted to pierce the outermost layer of the skin of the patient as best shown in FIGS. 17–19. The lower housing 20 is comprised of a non-stretchable, molded material such as polypropylene. The combination of lower housing 20 with the depression 25' surrounding device 2 in combination with the adhesive layer 30, comprise another example of a means for securing the housing 15, and the skin penetrating member 2 with the microprotrusions 4, on the skin of the patient.

The device 10 is generally comprised of battery 32, electronic circuitry 19,40, electrodes 22,24, counter reservoir 28, support member 15 housing donor reservoir 27, and skin penetrating device 2, all of which are integrated into a self-contained unit. Electrodes 22,24 and reservoirs 27,28 are retained by lower housing 20. The outputs (not shown in FIG. 15) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of reservoirs 27 and 28. The bottom side 46 of counter reservoir 28 contacts the patient's skin through the opening 29 in adhesive layer 30. The bottom side 46' of donor reservoir 27 contacts the patient's skin through the plurality of openings 8 in the skin penetrating device 2 as best shown in FIG. 3. The agent in donor reservoir 27 is typically in the form of a solution, most preferably an aqueous solution, which solution is contained in a solid matrix material such as a hydrophilic polymer matrix (e.g., a hydrogel) which allows free mobility of the agent therethrough. The reservoir matrix material fills the voids between the cross members 5 and the openings 8 in the sheet 6 (not shown in FIG. 15) such that the agent reservoir is in contact with the body surface as can best be seen in FIG. 3. As discussed above, a connecting medium can be placed as a layer on the skin-proximal side of sheet 6, with the microblades 4 passing therethrough. The optional connecting medium provides a more consistent agent flow pathway between the donor reservoir 27 and the skin. Typically the agent is present initially in both the reservoir and the connecting medium because of diffusion or because the reservoir and connecting medium are the same material.

The device 10 adheres to the patient's body surface (e.g., skin) by means of a peripheral adhesive layer 30 (which has upper adhesive side 34 and body-contacting adhesive side 36) and, optionally, anchoring elements on the device 2 of any of the embodiments discussed herein. Further, optionally, the connecting medium 65 can be tacky or adhesive for assisting in maintaining interface contact with the skin. The adhesive side 36 covers the entire underneath side of the device 10 except where the device 2 and counter electrode reservoir 28 are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and agent reservoirs within housing depression 25, 25' as well as retains device 2 to lower housing 20 and lower housing 20 to upper housing 16.

In one embodiment of the agent delivery/sampling device there is a release liner (not shown) on the device 10 for maintaining the integrity of adhesive layer 30 when the device is not in use. In use, the release liner is stripped from the device before the device is applied to the skin. Device 10 also has a push button switch 12, which when pressed turns the device 10 on which is made apparent to the user by means of LED 14 becoming lit. Agent is delivered through the patient's skin (e.g., on the arm) by electrotransport over a predetermined delivery interval.

Figure 20:
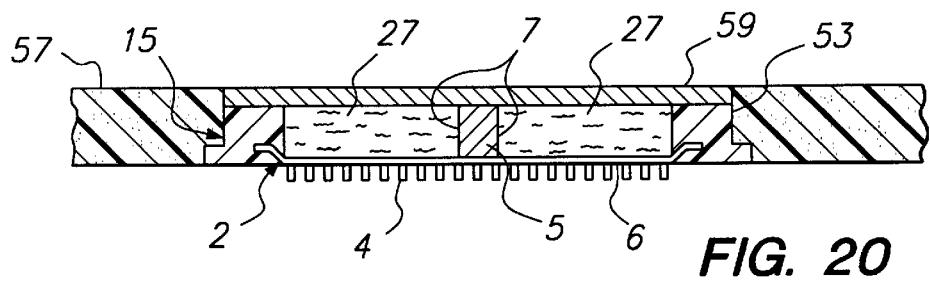
FIG. 20 is a diagrammatic cross-sectional view of a passive agent delivery/sampling system in accordance with one embodiment of the present invention.

In other embodiments of the present invention, passive transdermal delivery or sampling devices are used with housing 15 predisposed on the top (i.e., skin distal) surface of the member 6. It will be appreciated by those working in the field that the present invention can be used in conjunction with a wide variety of passive transdermal systems, as the invention is not limited in this regard. For examples of passive systems, reference may be had to, but not limited to, U.S. Pat. Nos. 4,379,454 to Campbell, et al., 4,588,580 to Gale et al., 4,832,953 to Campbell et al., 4,698,062 to Gale et al., 4,867,982 to Campbell et al., and 5,268,209 to Hunt et al., of which any of the disclosed systems can be used with the present invention. One example of a passive transdermal delivery/sampling device is illustrated in FIG. 20. Housing 15 having the edges of sheet member 6 embedded in the outer annular wall 53 thereof is housed in a foam pad 57 which can be applied (e.g., adhered) to the body surface. The edges of sheet member 6 need not be embedded in the outer annular wall, as the sheet member 6 can be attached to the housing 15 as described in the previous embodiments. Extending across annular wall 53 and cross-member 5 is a top 59. Top 59 is fixedly attached at either end to outer annual wall 53 and foam pad 57. The skin proximal surface of foam pad 57 is coated with adhesive and adheres to the skin. Thus, the combination of foam pad 57 and top 59 comprise yet another means for securing reservoir housing 15 to a patient's skin. The passive delivery/sampling device has a peripheral adhesive on the body-contacting surface of foam pad 57 and an adhesive interface gel (not shown) on the body-contacting side of the member 2.

It will be appreciated by those working in the field that the present invention can also be used in conjunction with a wide variety of osmotic and pressure driven systems, as the invention is not limited to a particular device in this regard. For examples of osmotic and pressure driven devices, reference may be had to U.S. Pat. Nos. 4,340,480 to Eckenhoff, 4,655,766 to Theeuwes et al., 4,753,651 to Eckenhoff, 5,279,544 to Gross et al., 4,655,766 to Theeuwes, 5,242,406 to Gross et al., and 4,753,651 to Eckenhoff any of which can be used with the present invention.

This invention has utility in connection with the delivery of agents within any of the broad class of drugs normally delivered through body surfaces and membranes, including skin. In general, this includes drugs in all of the major therapeutic areas. The invention is also useful in the transdermal delivery of proteins, peptides and fragments thereof, whether naturally occurring, chemically synthesized or recombinantly produced. The invention may additionally be used in conjunction with the delivery of vaccines, nucleotidic drugs, including oligonucleotide drugs, polynucleotide drugs, and genes. These substances typically have a molecular weight of at least about 300 daltons, and more typically have a molecular weight of at least about 300 to 40,000 daltons. As mentioned, the device 2 of the present invention can also be used with sampling devices including, but not limited to, reverse electrotransport (i.e., reverse iontophoresis and/or reverse electroosmosis in the case of sampling uncharged materials such as glucose), osmosis, and passive diffusion. For example, reference may be had to U.S. Pat. Nos. 4,756,314 to Eckenhoff et al., 5,438,984 to Schoendorfer, 5,279,543 to Glikfeld et al., and 5,362,307 to Guy et al. The invention will be further illustrated by the following specific examples.

Example 1

Hairless guinea pigs were anesthetized with ketamine/xylazine. The skin was washed with soap and water, dried and then wiped gently with an isopropyl alcohol pads. The skin of the animals was manually bidirectionally stretched and a foam housing (outer diameter of 3.8 cm, inner diameter of 1.6 cm and thickness of 1.6 mm) was applied to the stretched skin site. A microprotrusion array (a stainless steel sheet having a plurality of openings therein, a thickness of 25 $\mu$m, a microprotrusion length of 500 $\mu$m, a microprotrusion density of 72 microprotrusions/cm$^2$, and a skin-contact area of 2 cm$^2$ (circular shape, 1.6 cm diameter) was inserted into the center of the foam housing, microprotrusion side down. A hard plastic button (1.6 cm diameter) was placed on the skin distal side of the microprotrusion array. The microprotrusions were forced into the skin by folding the skin where the housing and microprotrusion array had been placed. The thumb was placed over the button and the index finger was below the flap of skin and directly below the microprotrusion array. Manual pressure (approximately 2 kg/cm$^2$) was applied for approximately 10 seconds. Each application type was performed in triplicate at every time point.

For the pretreatment, the microprotrusion array was removed after manual application and the release liner removed from the foam housing. The compartment was filled with either 350 $\mu$L of a gel comprised of an aqueous phosphate buffered saline solution containing 3% hydroxyethylcellulose (HEC gel) or a gel comprised of an aqueous phosphate buffered saline solution containing 23% polyvinylalcohol (PVOH gel). A release liner top (3.8 cm diameter) was adhered to the top of the foam housing. The animals were wrapped with Vetrap™ adhesive tape and allowed to recover until the end of their specified wearing time.

For the in situ treatment, the microprotrusion array was left in place after manual application. The release liner was removed from the foam housing and a hydrophilic porous sintered high density polyethylene matrix (2 cm$^2$ area, 1.6 cm diameter and a thickness of 1.6 mm (HDPE matrix) was placed against the skin distal side of the microprotrusion array. Phosphate buffered saline solution was pipetted into the compartment (250 $\mu$L). A release liner top was adhered to the top of the foam housing. The combination of the foam housing adhered to the skin and the release liner top adhered to the foam housing comprised a hold down means for securing the HDPE matrix securely against the microprotrusion array. The animals were wrapped with adhesive tape and allowed to recover until the end of their specified wearing time.

At the end of the wearing times (0, 0.5, 1, 2, and 24 hours), the wrapping and systems were removed. Excess gel or liquid was wiped away with a gauze pad. A cotton swab was imbibed with India ink (Higgins® Eternal Black India ink) until saturated. The treated sites were lightly stretched by hand and the dye liberally rubbed into the sites. The dye was applied in a circular motion, applying in two opposing directions for approximately 15 seconds. The excess dye was wiped off with a gauze pad. Isopropyl alcohol pads were then used to remove any dye from the skin until only the dyed microcuts/pathways created by the microprotrusion arrays were visible. Photographs were taken of the sites with a video scope. Subsequently, the animals were euthanized and the skin sites removed and frozen. Each frozen skin site was biopsied with an 8 mm biopsy punch. Biopsies were mounted onto a cryostat chuck and sectioned parallel to surface, first section at 20 $\mu$m, remainder at 50 $\mu$m. Thereafter, the individual skin sections were mounted onto microscope slides and individually dyed holes counted in each slice. From these data, and from the density of microprotrusions in the microprotrusion arrays, the percent of pathways that were dyed in a particular skin section can be calculated and plotted as a function of depth. Each data point represents the mean of three determinations with its associated standard error. The average depth at which 16%, 50% and 84% of the pathways are dyed ($D_{16}$, $D_{50}$, $D_{84}$) can also be extrapolated as well as their associated standard error.

Figure 22:
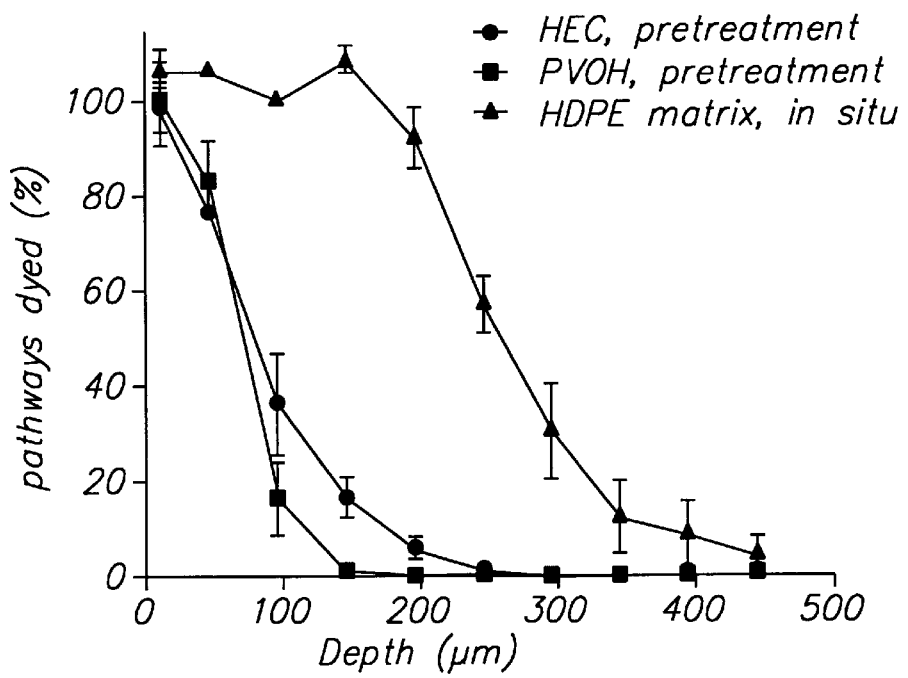
FIG. 22 is a graph showing the percent pathways dyed one hour after application of microprotrusion arrays into the skin of living hairless guinea pigs.

Penetration of the dye into the skin is an indication that the microprotrusions have penetrated the skin and that the pathways created are open. Therefore, this technique was used to evaluate penetration of the microprotrusions into the skin as well as pathway collapse as a function of time after application of the microprotrusion array. FIG. 22 shows the percentage of pathways dyed as a function of depth (i.e., depth as measured from the skin's outer surface) one hour after application of the microprotrusion array. FIG. 22 shows that when the microprotrusion array is left in situ, which is achieved with the use of the HDPE matrix and the securing overlay, the pathways are more open and are deeper than when microprotrusion array is applied and then removed from the skin (ie, use of the microprotrusion array as a pretreatment). This indicates that the HDPE matrix and the securing overlay are capable of maintaining the microprotrusions in skin-piercing relation to the skin and thereby delaying pathway closure.

Figure 23:
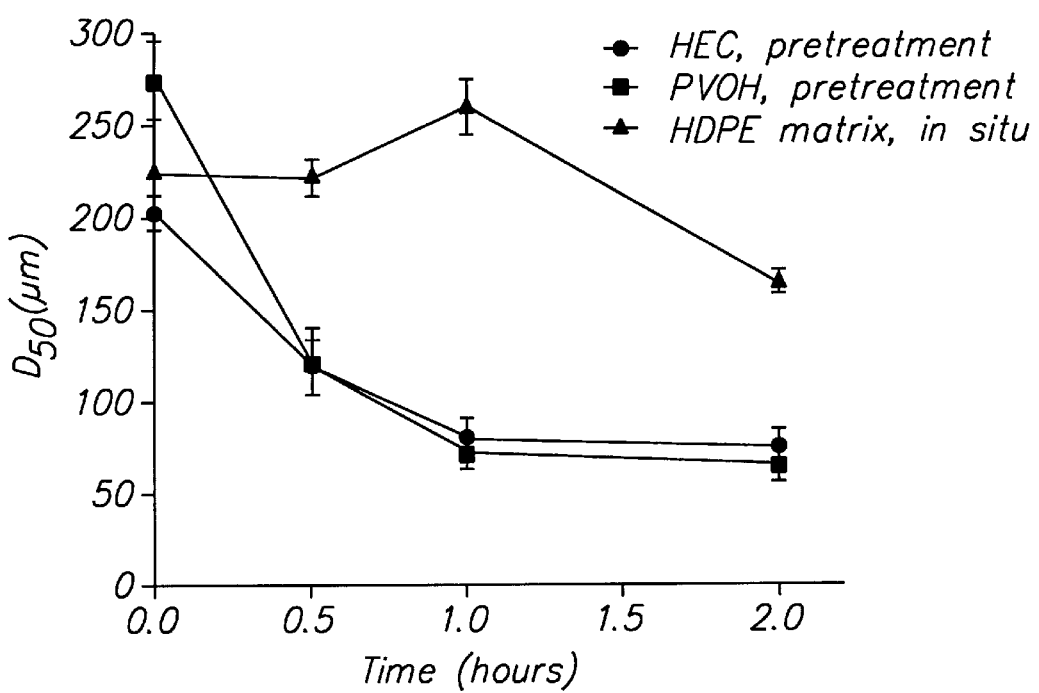
FIG. 23 is a graph showing pathway shutdown as a function of time after application of microprotrusion arrays into the skin of living hairless guinea pigs.
Figure 24:
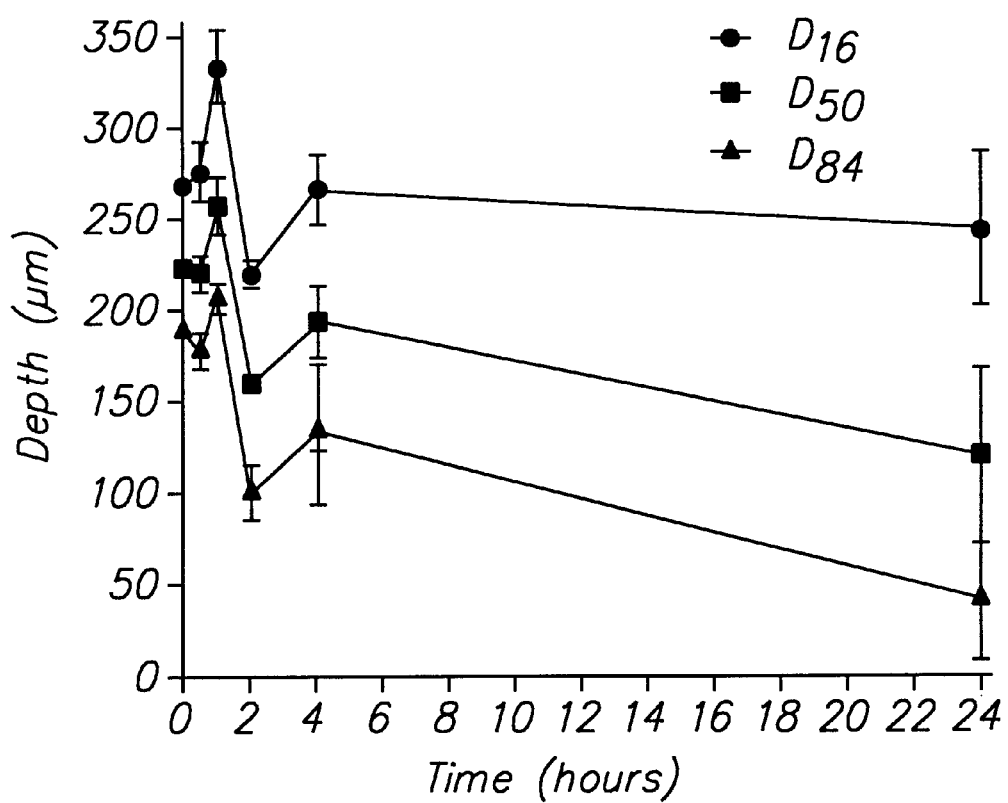
FIG. 24 is another graph showing pathway shutdown as a function of time after application of microprotrusion arrays into the skin of living hairless guinea pigs.

The kinetics of pathway collapse is illustrated in FIG. 23 by the plot of $D_{50}$ as a function of time after application of the microprotrusion array. These data show that pathway collapse occurs quickly (e.g., within the first hour) following pretreatment application of the microprotrusion array. Pathway collapse is inhibited when the microprotrusion array is left in situ, which is achieved with the use of the HDPE matrix and the securing overlay. This indicates that the HDPE matrix and the securing overlay maintain the microprojections in piercing relation to the skin, at a depth of more than 150 $\mu$m, for at least 2 hours. FIG. 24 shows the same kinetics obtained with the HDPE matrix for up to a 24 hour wearing time. After 24 hours, 50% of the pathways ($D_{50}$) are still open to a depth of about 150 $\mu$m.

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention is indicated by the appended claims rather than by the foregoing description, and all changes which come within the meaning and range of equivalents thereof are intended to be embraced therein.

What is claimed is:

1. A device for use in introducing or withdrawing an agent through a body surface, comprising:
   a body surface piercing member having a plurality of microprotrusions extending from a body surface proximal portion of the member, the microprotrusions being adapted to pierce the body surface to a depth of up to about 500 $\mu$m, a housing containing a reservoir for the agent to be introduced or withdrawn, the housing contacting and extending across a substantial portion of a body surface distal portion of the piercing member and maintaining the reservoir in agent-transmitting relation with the pierced body surface, the housing having a compressibility, in a direction normal to the body surface, of less than about 250 µm, and a securing member for securing the device to the body surface.

2. The device of claim 1, wherein the housing contacts and extends across the entire body distal portion of the piercing member.

3. The device of claim 1, wherein the securing member is selected from the group consisting of an adhesive overlay, a tape and a strap.

4. The device of claim 1, wherein the housing has a compressibilty of less than about 50 µm.

5. The device of claim 1, wherein the housing is comprised of a material selected from the group consisting of porous sintered polymers, open cell polymeric foams, porous polymer sheets, polymer screens, woven polymeric fabrics, porous ceramics, and a corrugated polymer sheet.

6. The device of claim 1, wherein the housing has sufficient flexibility to form a curved configuration in response to a hold down force applied by the securing member.

7. The device of claim 6, wherein the housing is comprised of a material selected from the group consisting of porous sintered polymers, open cell polymeric foams, porous polymer sheets, polymer screens, woven polymeric fabrics and a corrugated polymer sheet.

8. The device of claim 3, wherein the securing member comprises an adhesive.

9. The device of claim 8, wherein the adhesive is a skin contact adhesive.

10. The device of claim 1, wherein the housing is comprised of a plurality of sections, each section being substantially non-flexible in response to a hold down force applied by the securing means, the sections being hingedly attached to one another.

11. The device of claim 1, wherein the housing is comprised of porous sintered high density polyethylene.

12. The device of claim 1, wherein the housing is comprised of open cell polyurethane foam.

13. The device of claim 1, wherein the housing is comprised of open cell polyvinyl alcohol foam.

14. The device of claim 1, wherein the agent is a drug to be introduced into the body surface and the reservoir is a drug reservoir.

15. The device of claim 14, wherein the drug reservoir contains a transdermal drug formulation.

16. The device of claim 1, wherein the agent is a body analyte to be withdrawn from the body surface and the reservoir is an analyte collection reservoir.

17. The device of claim 16, wherein the body analyte is glucose.

18. The device of claim 1, wherein the piercing member comprises a sheet having a thickness of about 5 to 100 µm, the sheet having a plurality of openings therethrough, a body proximal surface adapted to be placed against the body surface and said plurality of microprotrusions extending from the body proximal surface.

19. The device of claim 18, wherein the sheet is comprised of metal.

20. The device of claim 19 wherein the metal is selected from the group consisting of stainless steel and titanium.

21. The device of claim 1, wherein the piercing member comprises a sheet having a thickness of about 5 to 100 µm, the sheet having a body proximal edge, with said plurality of microprotrusions, adapted to be placed against said body surface.

22. The device of claim 21, wherein the sheet is comprised of metal.

23. The device of claim 22, wherein the metal is selected from the group consisting of stainless steel and titanium.

24. The device of claim 21, wherein the housing comprises a plurality of said sheets.

25. The device of claim 1, wherein the microprotrusions are maintained in piercing relation to the skin surface of an animal during normal movement thereof.

26. The device of claim 1, wherein the housing has a honeycomb structure.

27. The device of claim 1, wherein the housing has a peripheral wall and at least one cross member.

28. The device of claim 27, wherein the housing has a plurality of cross members.

29. The device of claim 28, wherein adjacent cross members are separated by a distance of no more than about 4 times a distance separating adjacent microprojections on the piercing member.

* * * * *